(12) United States Patent
Smith

(10) Patent No.: US 11,041,793 B1
(45) Date of Patent: Jun. 22, 2021

(54) HYDROMETER TESTING AND FILTRATION APPARATUS

(71) Applicant: Mark Raymond Smith, Loudon, TN (US)

(72) Inventor: Mark Raymond Smith, Loudon, TN (US)

(*) Notice: Subject to any disclaimer, the term of this patent is extended or adjusted under 35 U.S.C. 154(b) by 449 days.

(21) Appl. No.: 16/150,476

(22) Filed: Oct. 3, 2018

Related U.S. Application Data

(60) Provisional application No. 62/567,274, filed on Oct. 3, 2017.

(51) Int. Cl.
| | |
|---|---|
| *G01N 9/14* | (2006.01) |
| *B01D 29/00* | (2006.01) |
| *G01N 33/14* | (2006.01) |
| *C12L 11/00* | (2006.01) |
| *G01N 9/36* | (2006.01) |
| *B01D 29/15* | (2006.01) |

(52) U.S. Cl.
CPC ............ *G01N 9/14* (2013.01); *B01D 29/0002* (2013.01); *B01D 29/15* (2013.01); *C12L 11/00* (2013.01); *G01N 9/36* (2013.01); *G01N 33/146* (2013.01)

(58) Field of Classification Search
CPC .......... G01N 9/14; G01N 33/146; G01N 9/36; B01D 29/15; B01D 29/0002; C12L 11/00
See application file for complete search history.

(56) References Cited

U.S. PATENT DOCUMENTS

| | | | | | |
|---|---|---|---|---|---|
| 1,415,385 | A | * | 5/1922 | Oswald | H02J 7/1492 290/35 |
| 2,198,351 | A | * | 4/1940 | Thielers | G01N 9/10 200/85 R |
| 3,597,973 | A | * | 8/1971 | Ryder | H01M 50/60 73/291 |
| 3,914,982 | A | * | 10/1975 | Zanetti | G01N 27/121 73/29.02 |
| 4,557,186 | A | * | 12/1985 | Brown | C12C 13/00 426/16 |

* cited by examiner

*Primary Examiner* — Nathaniel T Woodward
(74) *Attorney, Agent, or Firm* — Robinson IP Law, PLLC

(57) ABSTRACT

A multipurpose device used in fermenting wine as a filter for hydrometer testing, siphoning, and a cap punch is disclosed. The filtering device includes a perforated vessel, tubular in shape, with a flange which floats on the cap of the must or fermenting wine and stabilizes the filtering device within the primary fermenter, while the submersed portion of the vessel, below the flange, fills through perforations with liquids free of debris for testing, siphoning, or sampling; a multi-ringed siphoning attachment inserts into the tubular shaped vessel of the filtering device, snaps into place on the rim of the vessel, and securely holds a siphon hose in place within the primary fermenter for siphoning; and a handle which, when snapped into place on the rim of the filtering device, converts the foot of the filtering device to a cap punch.

16 Claims, 9 Drawing Sheets

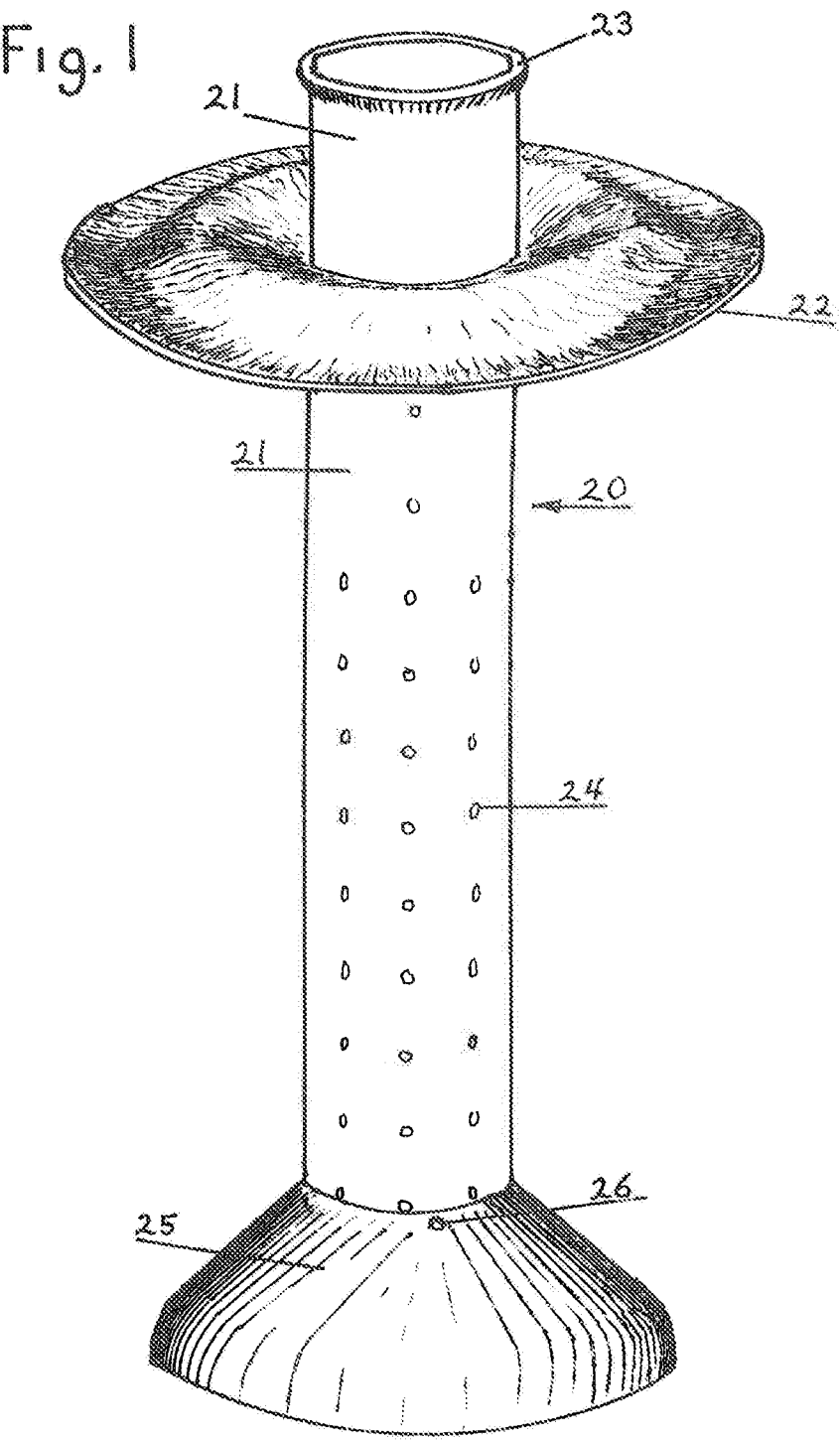

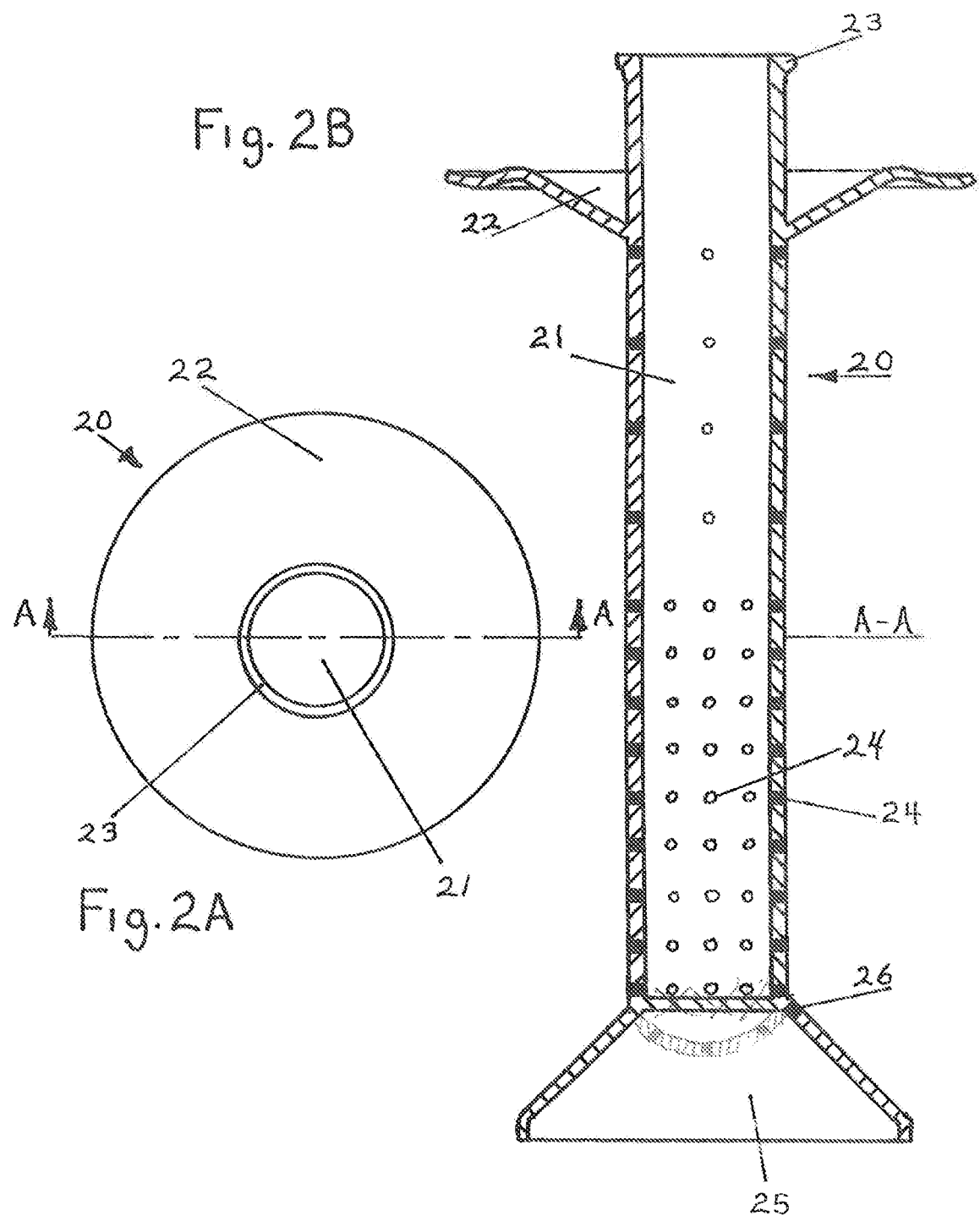

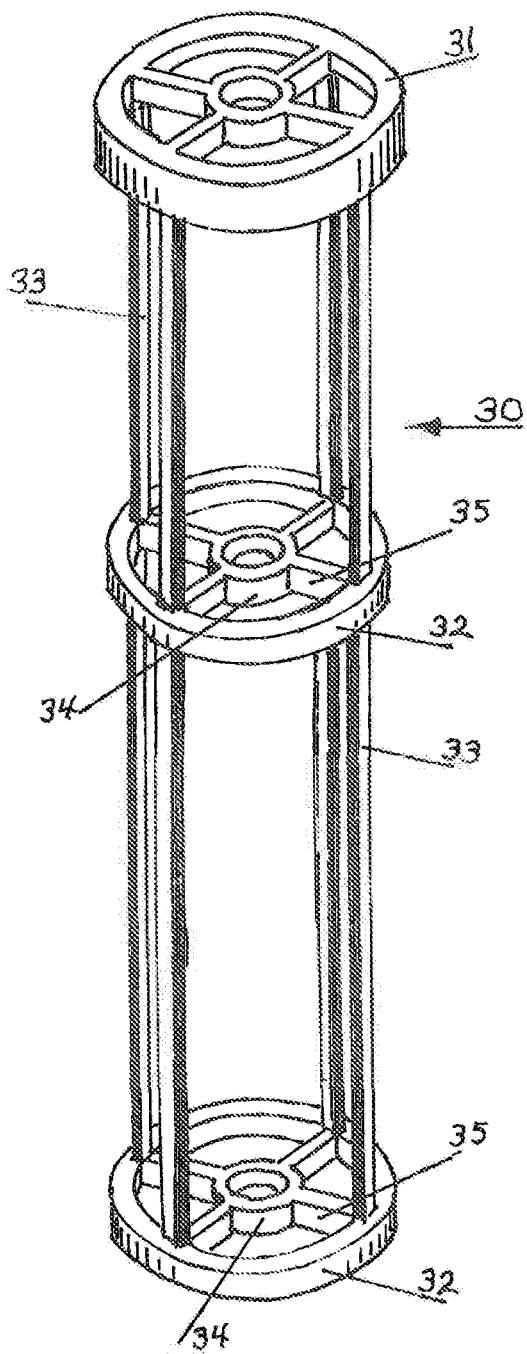

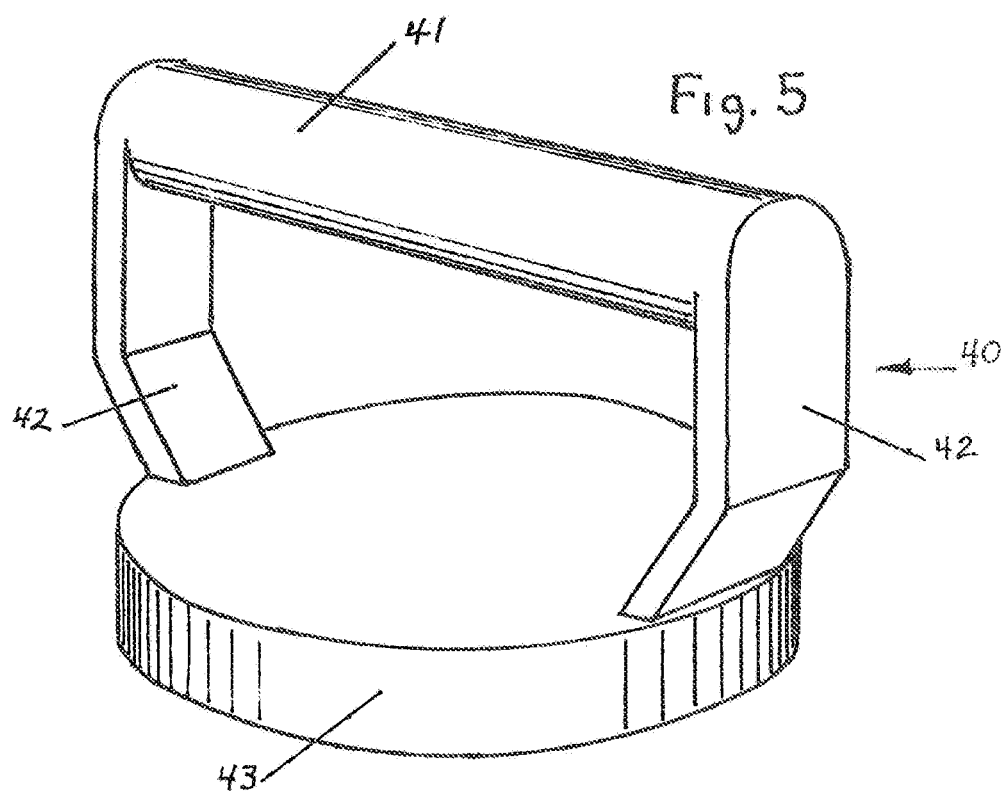

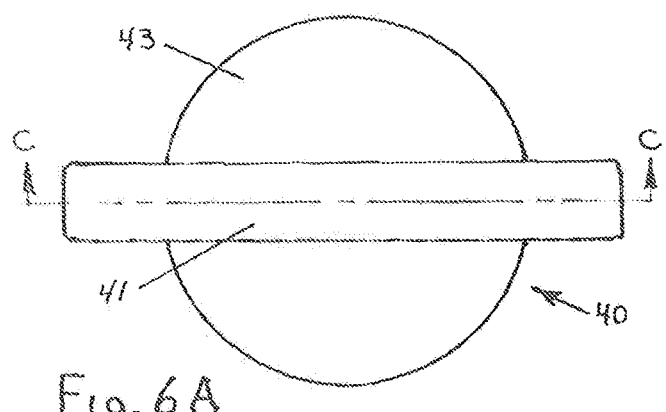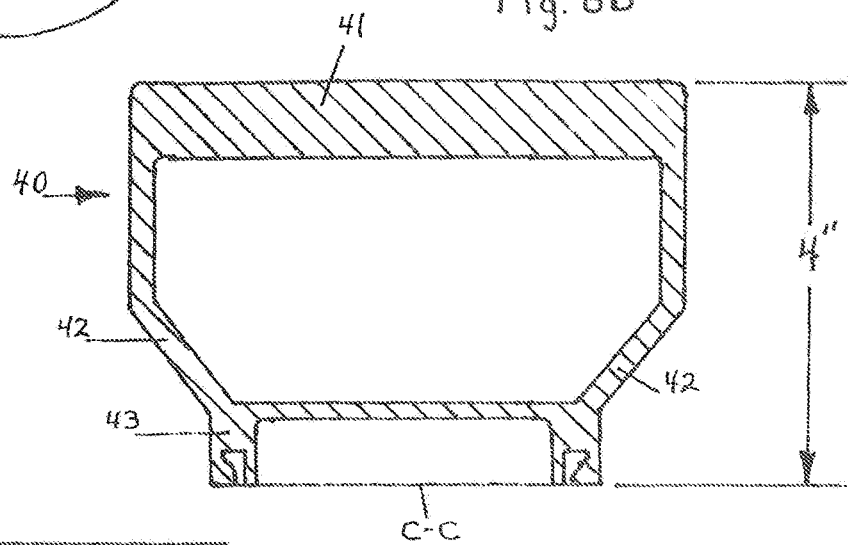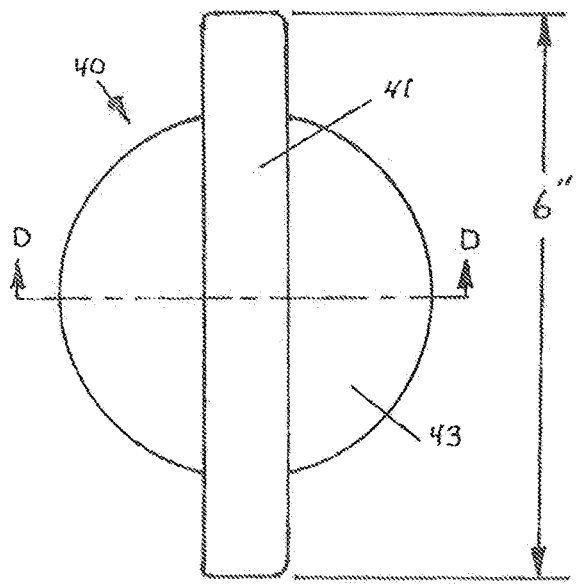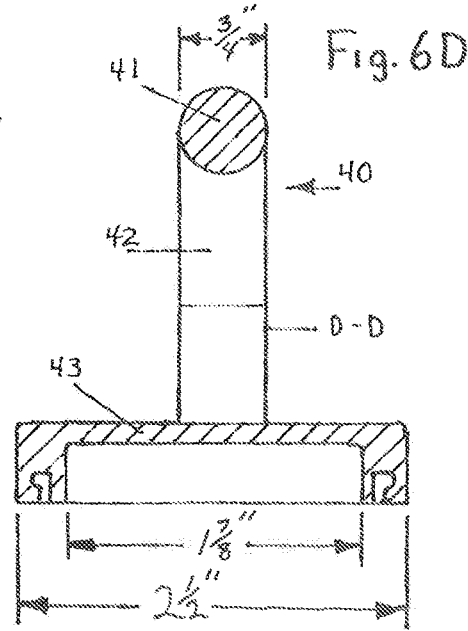

us 11,041,793 B1

HYDROMETER TESTING AND FILTRATION APPARATUS

CROSS-REFERENCE TO RELATED APPLICATION

This application claims priority to and is a non-provisional of U.S. Provisional Patent Application Ser. No. 62/567,274 for a "Fermenter's Friend" filed on Oct. 3, 2017, the contents of which are incorporated herein by reference in its entirety.

FIELD

The present invention relates generally to the making of fermented beverages. More particularly, the present invention relates to the making of wine and to the equipment and methods used when fermenting wine.

BACKGROUND

Since the invention of the hydrometer in 1790 the method of use has seen little change and the taking of hydrometer measurements when fermenting wine has become a standard practice used by winemakers to measure the level of fermentable sugars in freshly pressed juices and fermenting wines. A hydrometer floats in liquid to measure the specific gravity of the liquid. In wine making, the specific gravity of the must and fermenting wine is converted to BRIX. BRIX indicates the level of unfermented sugars in the liquid. Sugar levels of the must should be checked before the fruit juice starts to ferment. The resulting BRIX reading of the unfermented juice is used to generally indicate the expected alcohol content of the finished wine. This allows for the manipulation of finished alcohol content in wine by controlling sugar levels before and in the early stages of fermentation. The BRIX is also checked at regular intervals during fermentation. As the wine ferments the unfermented sugars are converted to alcohol until BRIX drops to zero, the indicator that fermentation is complete. Each time the BRIX is measured samples are extracted, free of skins, seeds, pulp and foam which can skew hydrometer readings, from the primary fermenter, a little at a time using a wine thief, meat baster, measuring cup, or ladle, to a testing container until the hydrometer floats. Small samples of liquid for other testing, such as acid levels and PH, are also extracted from the primary fermenter. Since fermentation generates heat the temperature of the fermenting wine in the primary fermenter is also checked regularly during fermentation.

At the end of fermentation the fermented wine is separated from the cap and lees in the primary fermenter to carboys, as free of crushed fruit and lees as possible, by siphoning, pressing, or both. Siphoning often results in grape skins, seeds, and pulp being drawn into the open end of the siphon hose or racking cane. When plugged the siphon tube must be removed from the primary fermenter and cleared of debris, then re-sterilized before siphoning can continue. This can happen a number of times during a single siphon process. During siphoning the position of the open end of the siphon tube within the primary fermenter must be manually controlled to prevent plugging or the extraction of unwanted seeds, sediment, or foam. The siphon hose is sometimes secured to the outside of the primary fermenter with tape for added control.

Both of the processes described above result in drips, runs, or spills of staining liquids from the removal of plugged siphon tubes and from repeatedly dipping instruments in and out of the primary fermenter to extract samples to a testing container for hydrometer or other measurements.

Additionally, both of the processes described above expose the must or fermenting wine unnecessarily to open air and bacterial contaminants due to the repeated insertion and removal of instruments into the primary fermenter and the length of time required to complete each process, during which time the primary fermenter is left uncovered. Exposure to open air should be minimized as much as is practically possible throughout the fermentation process. Air generates the growth of unwanted bacteria in the primary fermenter.

During the fermentation of wine with a cap of fruit skins, the skins must be "punched" into the fermenting wine regularly to help prevent bacteria from forming on the cap and to put the skins in contact with the fermenting wine, which acids color and flavor. Any number of objects may be used, from a drinking glass to a stainless cook pan, to punch down the cap.

SUMMARY

Therefore, it is the object of the present invention to provide a multipurpose device which eliminates the extraction of samples from the primary fermenter for hydrometer readings, eliminates the aggravation of plugged siphoning tubes, minimizes the mess made while performing these necessary tasks, significantly reduces the exposure of the must or fermenting wine to open air and bacterial contaminants through process efficiencies, and provides a handy tool to use as a cap punch.

Accordingly, a filtering device is provided which includes a perforated vessel, tubular in shape, with a flange which floats and stabilizes the filtering device on the cap of must or fermenting wine in the primary fermenter. The submersed portion of the vessel, below the flange, fills through the perforations in the vessel with liquids free of crushed fruit or lees for testing, siphoning, or sampling. A multi-ringed siphoning attachment inserts into the tubular shaped vessel of the filtering device and snaps into place on the rim of the vessel. When joined the filtering device securely holds the siphon attachment in place within the primary fermenter and provides a continuous reservoir of filtered wine for siphoning from the primary fermenter. A handle attachment snaps into place on the rim of the vessel of the filtering device to convert the foot of the filtering device to a cap punch.

The three components of the present invention are the filtering device as shown in FIG. 1 and FIG. 2, the siphoning attachment as shown in FIG. 3 and FIG. 4 and the handle attachment as shown in FIG. 5 and FIG. 6. The following relationships exist between these three components.

The filtering device may be used independently to provide a pool of filtered liquid for testing. The filtering device is also used in conjunction with the siphoning attachment or the handle attachment. The siphoning attachment holds a siphon hose, inserts into the filtering device, and snaps into place for siphoning. The handle attachment snaps into place on the filtering device to convert the filtering device into a cap punch.

The handle attachment and the siphoning attachment have no relationship. The siphoning attachment has no independent function. The handle attachment has no independent function.

In a first aspect, a hydrometer filter includes: an elongate vessel having a top end and a bottom end that is distal from the top end, the elongate vessel having an inner portion including an open top end and a closed bottom end, the elongate vessel further comprising a plurality of perforations formed therethrough the perforations sized to allow fluid to enter the elongate vessel; and a flange located concentrically around the vessel, the flange located proximate to the top end of the elongate vessel. The hydrometer filter is shaped to receive a hydrometer through the open top end of the elongate vessel and to support the hydrometer within a fermentation container for testing of a fluid within the fermentation container.

In one embodiment, the hydrometer filter further includes a foot formed on the bottom end of the elongate vessel, wherein the foot has a diameter that is greater than a diameter of the elongate vessel. In another embodiment, the hydrometer filter further includes a vent hole formed through the foot.

In yet another embodiment, the flange is removably attached around the elongate vessel. In one embodiment, the flange is integrally formed on the elongate vessel. In another embodiment, an inner diameter of the vessel tapers in width towards a top end of the vessel. In yet another embodiment, the flange further includes a raised ring formed around the flange.

In one embodiment, the hydrometer filter further includes a handle removably attached to the filter. In another embodiment, the handle is attached to the filter at the flange. In yet another embodiment, the flange further comprising one or more apertures formed therethrough, the one or more apertures shaped to receive connectors formed on ends of the handle.

In one embodiment, the elongate vessel is cylindrical. In another embodiment, the perforations have a diameter of approximately ⅛ inches.

In yet another embodiment, the hydrometer filter further includes a siphon tube holder having: a first clamping member having a first pad located thereon; a second clamping member having a second pad located thereon and one or more retention portions located on an end of the second clamping member; and a spring located between the first clamping member and the second clamping member such that the first pad is biased towards the second pad.

In a second aspect, a hydrometer filter includes: an elongate vessel having a top end and a bottom end that is distal from the top end, the elongate vessel having an inner portion including an open top end and a closed bottom end, the elongate vessel further comprising a plurality of perforations formed therethrough, wherein the perforations are sized to allow fluid to enter the elongate vessel; a flange located concentrically around the vessel, the flange located proximate to the top end of the elongate vessel; a foot formed on the bottom end of the elongate vessel, wherein the foot has a diameter that is greater than a diameter of the elongate vessel. The hydrometer filter is shaped to receive a hydrometer through the open top end of the elongate vessel and to support the hydrometer within a fermentation container for testing of a fluid within the fermentation container.

In one embodiment, the hydrometer filter further includes a vent hole formed through the foot.

In a third aspect, a hydrometer filter includes: an elongate vessel having a top end and a bottom end that is distal from the top end, the elongate vessel having an inner portion including an open top end and a closed bottom end, the elongate vessel further comprising a plurality of perforations formed therethrough, wherein the perforations are sized to allow fluid to enter the elongate vessel; a flange located concentrically around the vessel, the flange located proximate to the top end of the elongate vessel; a foot formed on the bottom end of the elongate vessel, wherein the foot has a diameter that is greater than a diameter of the elongate vessel; and a handle removably attached to the filter. The hydrometer filter is shaped to receive a hydrometer through the open top end of the elongate vessel and to support the hydrometer within a fermentation container for testing of a fluid within the fermentation container.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

FIG. 1 is a perspective view of the filtering device according to one embodiment of the present disclosure;

FIG. 2A is a top view of the filtering device shown in FIG. 1 according to one embodiment of the present disclosure;

FIG. 2B is a sectional view taken along lines A-A in FIG. 2A according to one embodiment of the present disclosure;

FIG. 3 is a perspective view of the siphoning attachment according to one embodiment the present disclosure;

FIG. 5 is a perspective view of the handle attachment according to one embodiment of the present disclosure;

FIG. 6A is a top view of the handle attachment shown in FIG. 5 according to one embodiment of the present disclosure;

FIG. 6B is a sectional view taken along lines C-C in FIG. 6A according to one embodiment of the present disclosure;

FIG. 6C is a top view of the handle attachment shown in FIG. 5 according to one embodiment of the present disclosure;

FIG. 6D is a sectional view taken along lines D-D in FIG. 6C according to one embodiment of the present disclosure;

DETAILED DESCRIPTION

Figure 4A:
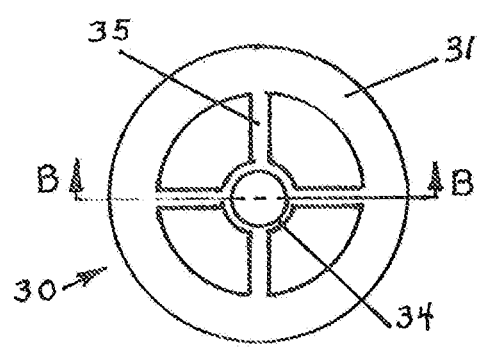
FIG. 4A is a top view of the siphoning device shown in FIG. 3 according to one embodiment of the present disclosure.

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Referring now in more detail to the filtering device of the present disclosure, in FIG. 1 and FIG. 2 there is shown a floating filter 20 having a vessel 21, a flange 22, a lipped rim 23, perforations 24, a foot 25, and an air hole 26. The floating filter 20 is used independently to provide a reservoir of liquid within a primary fermenter, clear of free-floating debris, for hydrometer measurements, temperature readings, or sampling. The floating filter 20 may also optionally be used in conjunction with a siphoning attachment, shown in FIG. 3 and FIG. 4, and a handle attachment, as shown in FIG. 5 and FIG. 6.

In more detail, still referring to FIG. 1 and FIG. 2, for taking hydrometer readings, a hydrometer is placed in the vessel 21 of the floating filter 20. The foot 25 of the floating filter 20 is inserted through a cap floating in the primary fermenter to submerse that portion of the vessel 21 with perforations 24, located below the flange 22, into the body of the must or fermenting wine until the flange 22 rests on top of the cap. The vessel 21 naturally fills with the filtered liquid up to the level of the liquids in the primary fermenter and floats the hydrometer to read the specific gravity and measure the BRIX.

In further detail, still referring to FIG. 1 and FIG. 2, shown is a floating filter 20 with a vessel 21 that has a diameter and length sufficiently large enough, such as about two inches in diameter and about twelve inches long, to accommodate the floating of a standard hydrometer and to allow the majority of the perforations 24 in the vessel 21 to reach through the cap in the primary fermenter and be primarily positioned in the main body of the fermenting liquid, below the cap and above sediment. The bottom of the tubular shaped vessel 21, where it joins the foot 25, has a solid surface, with no perforations 24, to prevent the lees from drawing into the vessel 21 from the bottom of the primary fermenter during siphoning.

The attached flange 22 is positioned around the outside diameter of and perpendicular to the vessel 21 about one inch down the lipped rim 23. The flange 22 is sufficiently wide enough, such as about one to two inches wide, to support the floating filter 20 on top of the cap in the primary fermenter and to provide stability to the floating filter 20 as it rests on a skin cap or foam. The flange 22 is slightly arched from its inside diameter where it rises from the outside diameter of the vessel 21, then curves downward as it nears its outside edge thus creating an air pocket for the floating filter 20. The angle of the arch is also designed to provide a good line of sight into the vessel 21 for reading the hydrometer floating inside. The flange 22 is flared slightly upward about one-half inch at its outside edge to help prevent tipping and the collection of foam or liquid in or around the flange 22.

The perforations 24 are of a sufficient number, such as from about 60 to about 120, and preferably approximately eighty-eight, and sufficient size, such as about one-eighth inch, to allow for quick and continual filling of the vessel 21, especially when siphoning, while filtering out particles that could plug a siphon hose or interfere with accurate hydrometer readings. Starting near or below the flange 22 about sixteen perforations 24 are evenly spaced around the vessel 21 in four vertical rows extending from the bottom of the flange 22 and down the vessel 21 about four inches. The number of the vertical rows of perforations 24 in the vessel 21 then doubles from four evenly spaced vertical rows to eight evenly spaced vertical rows which continue on down the vessel 21 to the top of the foot 25, thus positioning the greatest number of perforations 24, such as about seventy-two, in the clearest body of the fermenting liquid, below the cap and above the lees. The above description of locations and sizes of perforations may vary.

The foot 25 has a diameter at the bottom edge sufficiently large enough, such as about four inches, to provide stabilization of the floating filter 20 once the level of the contents of the primary fermenter drops the foot 25 to the layer of lees in the bottom of the fermenter during siphoning. The foot 25 bevels inward from the bottom edge of the foot 25 and upward about three inches to the top edge of the foot 25. The diameter of the foot narrows upward to the outside diameter of the bottom of the vessel 21, or about two inches. The beveled foot 25 has an open bottom to minimize the disturbance of the lees when it comes to rest in the bottom of the primary fermenter during siphoning. A small air hole 26 at the upper edge of the foot 25 allows any air to escape that might be trapped under the foot 25 as it is inserted through the cap.

The manufacturing details of the present invention as shown in FIG. 1 and FIG. 2 are that the floating filter 20 would be made of clear high-density polyethylene ("HDPE") plastic by a manufacturer of injection molded plastic products, preferably in a single mold. The floating filter 20 could be made in a larger size for commercial use.

Additionally, still referring to FIG. 1 and FIG. 2, the floating filter 20 could be used with any liquid in which a hydrometer is needed for a specific measurement. A hydrometer should be free from contact with any free floating matter or foam that would alter the reading. The present invention enables the use of a hydrometer under such conditions. The floating filter 20 could be used as a filter to aid in the siphoning of any liquid that may contain debris large enough to plug the siphoning hose being used. The floating filter 20 could be used for measuring the temperature of the fermenting wine, and for extracting small samples for testing acid levels or PH. The floating filter 20 could be used for brewing beer.

Referring now in more detail to the siphoning attachment of the present invention, in FIG. 3 and FIG. 4 there is shown a siphon hose insert 30 having an insert cap 31, two outer rings 32, eight outer ring connectors 33, three inner rings 34, and twelve inner ring connectors 35. The siphon hose insert 30 is used in conjunction with the filtering device shown in FIG. 1 and FIG. 2 to serve as a tool for siphoning from the primary fermenter to carboys.

In more detail, still referring to FIGS. 3 4, for siphoning from the primary fermenter to carboys, feed a siphoning hose, first through the inner ring 34 of the insert cap 31, then through the two remaining inner rings 34 of the siphon hose insert 30. Pull the hose through the bottom inner ring 34 about two inches. Insert the siphon hose insert 30, shown in FIG. 3 and FIG. 4, into the floating filter 20, shown in FIG. 1 and FIG. 2. Snap the insert cap 31 of the siphon hose insert 30 onto the lipped rim 23 of the floating filter 20. The beveled foot 25 of the floating filter 20 is inserted through the cap in the primary fermenter submersing that portion of the vessel 21 with perforations 24, located below the flange 22, into the body of the must or fermenting wine until the flange 22 rests on top of the cap. The vessel 21 fills with filtered liquid, Begin siphoning. The vessel 21 quickly replenishes the reservoir of filtered liquid as the wine is siphoned from the primary fermenter.

In further detail, still referring to FIG. 3 and FIG. 4, the siphon hose insert 30 has a diameter slightly smaller than the diameter of the floating filter 20, shown in FIG. 1 and FIG. 2, to allow for easy but secure insertion of the siphon hose insert 30 into the floating filter 20, such as about one and seven-eight inches. The siphon hose insert 30 is of sufficient length to allow snapping the insert cap 31 securely onto the lipped rim 23 of the floating filter 20 as shown in FIG. 1 and FIG. 2, such as about ten inches long.

The insert cap 31 of the siphon hose insert 30 snaps into place over the lipped rim 23 of the floating filter 20, shown in FIG. 1 and FIG. 2, and is of a sufficient diameter, such as about two and one-fourth inches, to securely hold the siphon hose insert 30 in place within the floating filter 20 during the siphoning of fermented liquids from the primary fermenter to carboys.

The three inner rings 34 are of a sufficient diameter, such as one-half inch, to allow for insertion of a siphon hose commonly used by winemakers and brewers for siphoning, but still securely hold the siphon hose in place.

The two outer rings 32 are of a diameter slightly smaller than the inside diameter of the floating filter 20 shown in FIG. 1 and FIG. 2, such as about one and seven-eighth inches, to allow for easy but secure insertion of the siphon hose insert 30 into the floating filter 20. The outer rings 32 are wide enough to provide stability and durability to the siphon hose insert 30, such as about one-quarter inch.

The outer ring connectors 33 extend vertically to join the insert cap 31 and the two outer rings 32. There are eight outer ring connectors 33, four outer ring connectors 33 about four inches long connect the insert cap 31 and middle outer ring 32, and four outer ring connectors 33 about five inches long connect the middle and bottom outer rings 32. The outer ring connectors 33 are evenly spaced around the inside diameter of the outer rings 32 and insert cap 31. The outer ring connectors 33 are of sufficient size to provide stability and durability to the siphon hose insert 30, such as about one-quarter inch wide and one-eighth inch thick.

The inner ring connectors 35 extend horizontally from the outside diameter of inner rings 34 to join an inner ring 34 to the outside diameter of the insert cap 31. There are twelve inner ring connectors 35. Four inner ring connectors 35 join one of the three inner rings 34 to the insert cap 31. Four inner ring connectors 35 connect one of the two remaining inner rings 34 to one of the two outer rings 32. The four inner ring connectors 35 are evenly spaced around the outside diameter of the inner rings 34 and the inside diameter of the insert cap 31 and the two outer rings 32. The inner ring connectors 35 are of sufficient size to provide stability and durability to the siphon hose insert 30, such as about one-quarter inch wide and one-eighth inch thick.

The manufacturing details of the present invention as shown in FIG. 3 and FIG. 4 are that the siphon hose insert 30 would be made of HDPE plastic by a manufacturer of injection molded plastic products, in a single mold if possible. Alternate versions of the siphon hose insert 30 could be made with various sized inner rings 34 to accommodate the different diameters of the siphon hoses most commonly used by winemakers and brewers. The siphon hose insert 30 could be made in a larger size for commercial use.

Additionally, still referring to FIG. 3 and FIG. 4, the siphon hose insert 30 could be used to aid in the siphoning of any liquid that may contain debris large enough to plug the siphoning hose being used. The siphon hose insert 30 could be used in brewing beer.

Referring now in more detail to the handle attachment of the present invention, in FIG. 5 and FIG. 6 there is shown a cap punch 40, a grip 41, two grip connectors 42, and a handle cap 43. The handle attachment, shown in FIG. 5 and FIG. 6, works in conjunction with the floating filter 20, shown in FIG. 1 and FIG. 2, to convert the foot 25 of the floating filter 20 to a cap punch tool. The handle attachment has no independent function.

In more detail, still referring to FIG. 5 and FIG. 6, the handle cap 43 snaps securely into place on the lipped rim 23 of the floating filter 20 as shown in FIG. 1 and FIG. 2 to use the foot 25 of the floating filter 20 as a cap punch 40.

In further detail, still referring to FIG. 5 and FIG. 6, the cap punch 40 has a diameter sufficient to allow it to snap securely in place on the lipped rim 23 of the floating filter 20 as shown in FIG. 1 and FIG. 2, such as about two and one-fourth inches. The grip connectors 42 extend upward and outward at an angle from each side of the handle cap 43 about one inch, then vertically, upward about one inch to the grip 41. The grip 41 is of a size sufficient to allow the user's hand to reach comfortably around the grip 41, such as about one-half inch wide and about four inches long.

The manufacturing details of the present invention as shown in FIG. 5 and FIG. 6 are that the cap punch 40 would be made of HDPE plastic by a manufacturer of injection molded plastic products, in a single mold if possible.

Figure 4B:
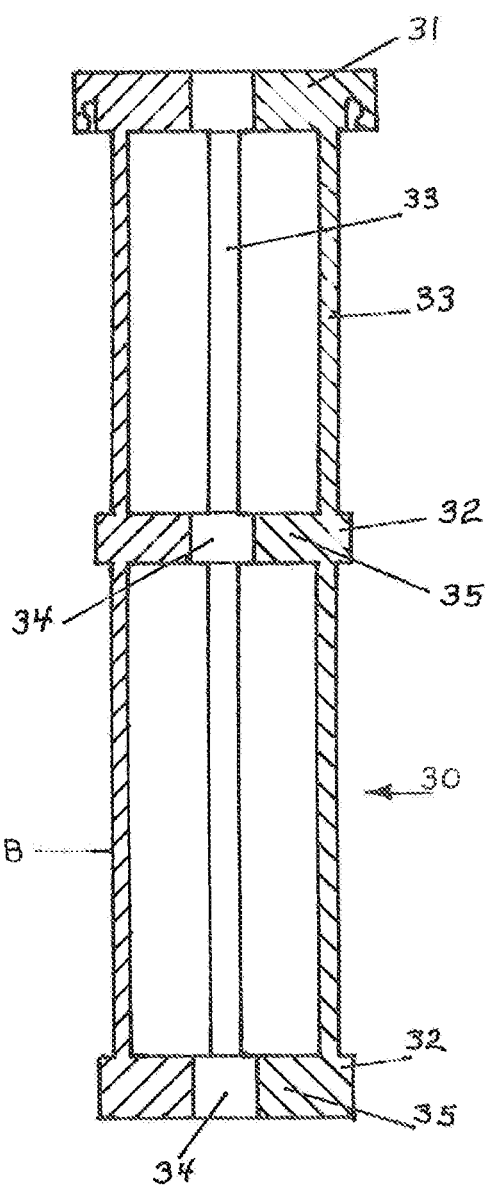
FIG. 4B is a sectional view taken along lines B-B in FIG. 4A according to one embodiment of the present disclosure.

Referring now in more detail to FIG. 2B, FIG. 4B, FIG. 6B and FIG. 6D, the snap on cap feature of the insert cap 31 of the siphon hose insert 30 as shown in FIG. 4B and of the handle cap 43 of the cap punch 40 as shown in FIG. 6B and FIG. 6D are identical in design. Each cap, 31 and 43, snaps over the lipped rim 23 of the floating filter 20 as shown in FIG. 2B for independent purposes, siphoning and punching. The design shown is one of many variations that exist for attaching a cap to a cylindrical container and serves only as an example. The final design of this feature will be determined with the assistance of the manufacturer.

Figure 7:
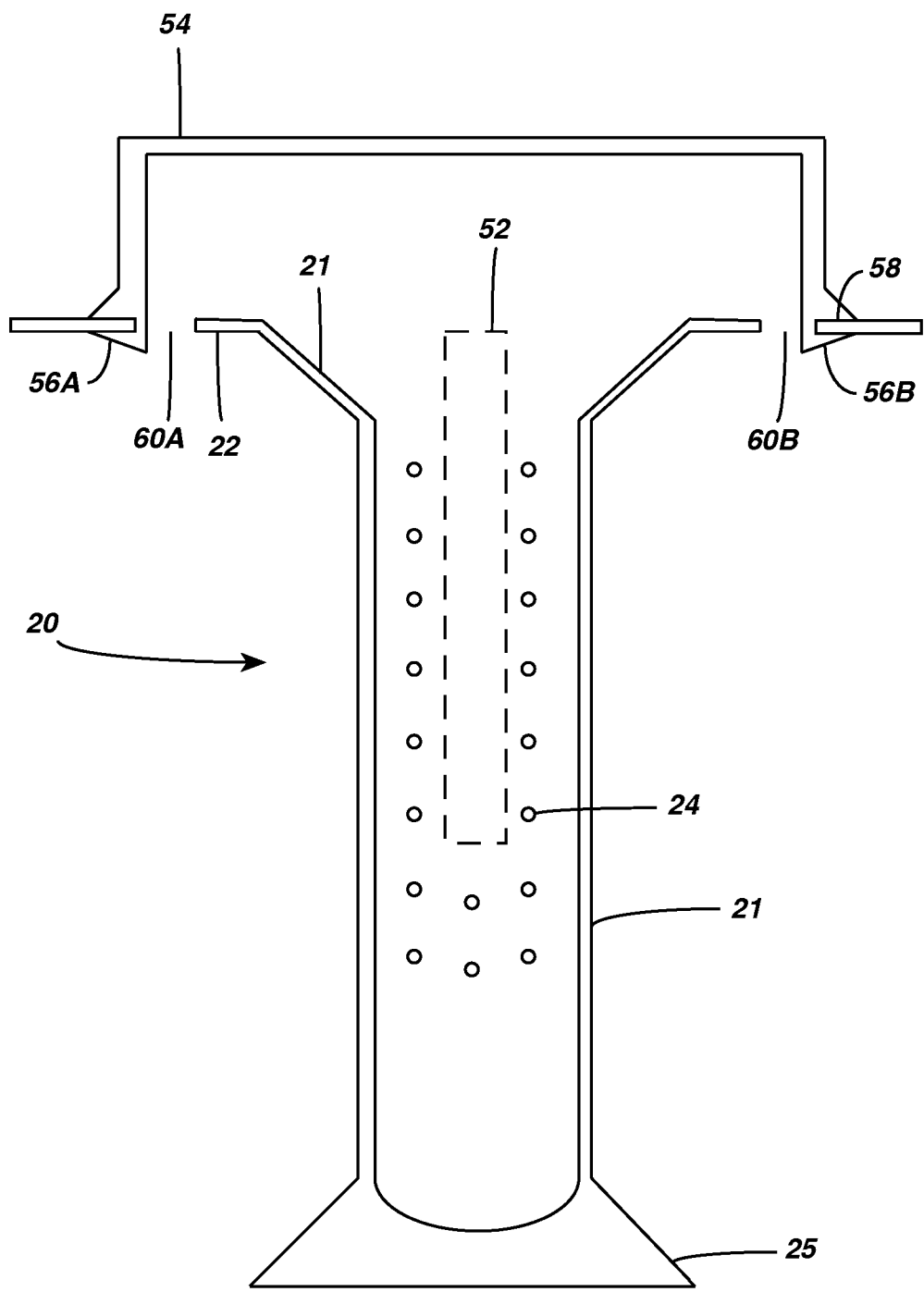
FIG. 7 is a cross-sectional side view of a filtering device including a removable handle according to one embodiment of the present disclosure.

Referring now to FIG. 7, in one embodiment the filter 20 includes the vessel 21 and flange 22, wherein the flange 22 is located at an upper end of the vessel 21. The flange 22 and upper end of the vessel 21 are integrally formed such that a tapered section 50 is formed at the upper end of the vessel 21. The tapered section 50 formed at the upper end of the vessel 21 allows a user to view at least a portion of a hydrometer 52 that is located within the vessel 21.

Figure 8:
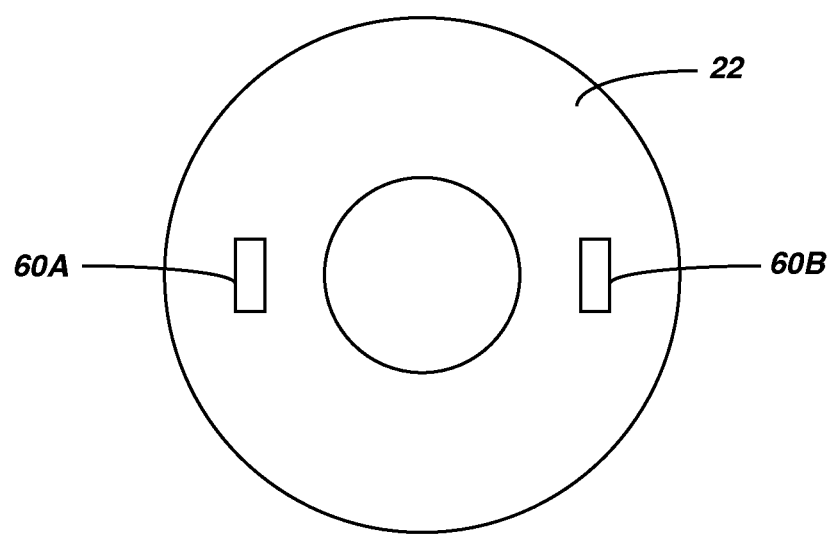
FIG. 8 is a top view of a flange of a filtering device according to one embodiment of present disclosure.

With further reference to FIG. 7, in one embodiment a handle 54 is shaped to be removably attached to the flange 22. The handle 54 includes connectors 56A and 56B formed on ends of the handle 54 for engaging the flange 22 and securing the handle 54 to the flange 22 and the filter 20. The connectors 56A and 56B are preferably shaped such that a slot 58 is formed in the connectors 56A and 56B, the slot 58 having a thickness such that the slot 58 conforms to a thickness of the flange 22. To attach the handle 54 to the flange 22, the connectors 56A and 56B are inserted through apertures 60A and 60B (FIG. 8) formed through the flange 22. The apertures 60A and 60B are preferably spaced apart at a distance that is equal to or less than a width of the connectors 58A and 58B such that when the connectors 58A and 58B are inserted the connectors 58A and 58B are urged resiliently outward to capture the flange 22 with the connectors 58A and 58B. To release the handle 54, a user squeezes sides of the handle 54 to release the connectors 58A and 58B from the flange.

Figure 9A:
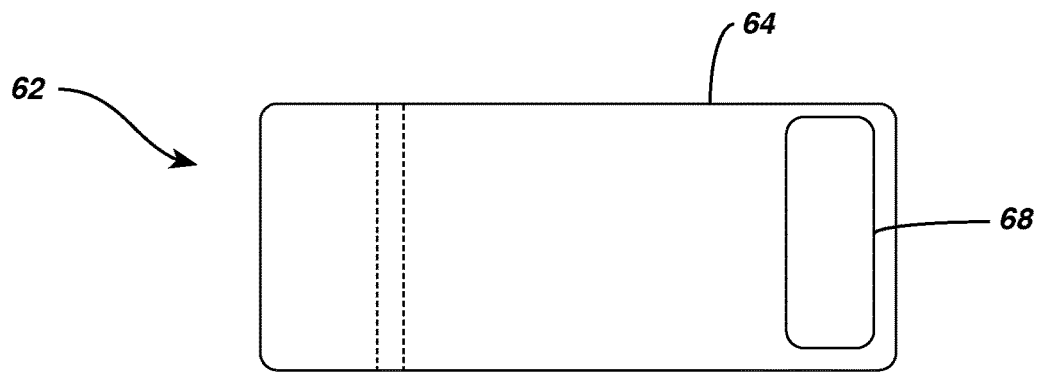
FIGS. 9A-9C show views of a siphon tube holder according to one embodiment of the present disclosure.
Figure 9B:
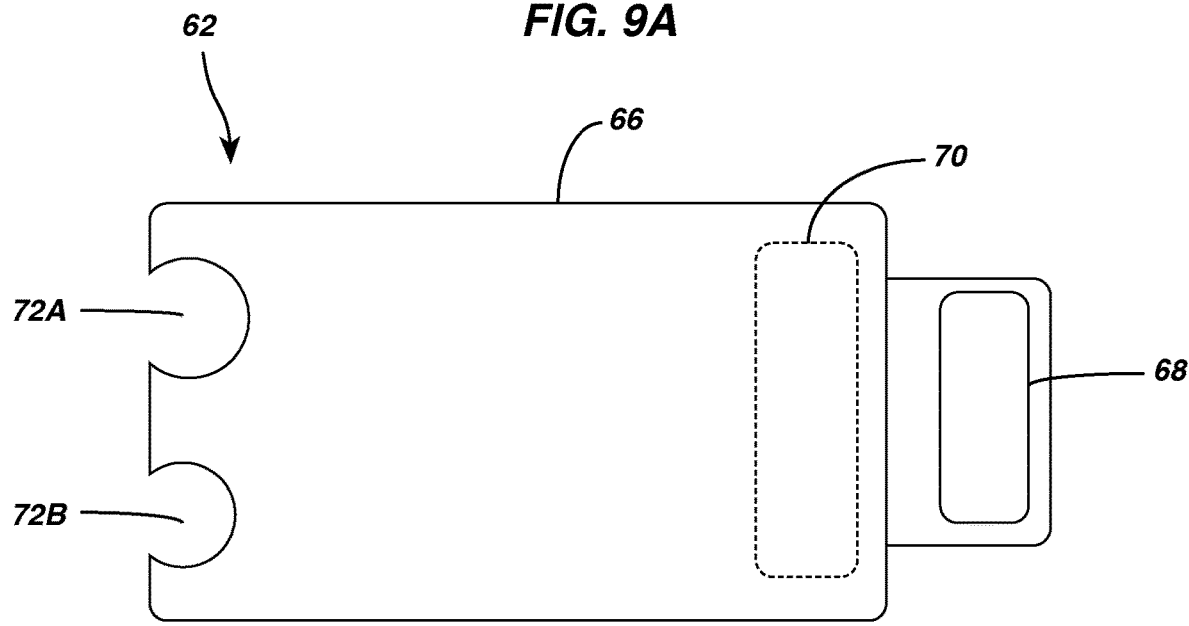
Figure 9C:
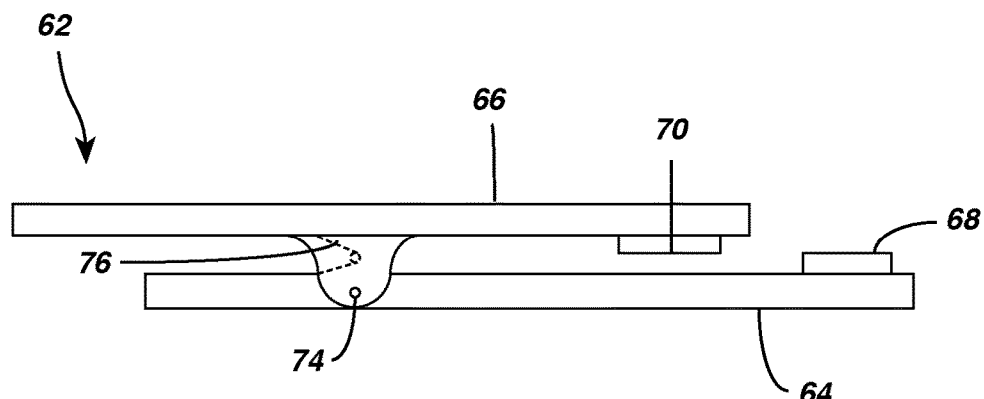

Referring now to FIG. 9A-9C, in one embodiment a siphon tube holder 62 is provided for maintaining a position of a siphon tube relative to a fermentation container and the filter 20. The siphon tube holder 62 includes a first clamping member 64 and an opposing second clamping member 66. The first clamping member 64 and second clamping member 66 are preferably elongate and planar in shape. The first clamping member 64 includes a first pad 68 at an end of the first clamping member 64 and the second clamping 66 includes a second pad 70 at an end of the second clamping member 66. The first pad 68 and second pad 70 are located such that the first pad 68 and second pad 70 contact opposite of an inner and outer wall of the fermentation container.

The siphon tube holder 62 includes one or more retention portions 72A and 72B formed on an end of the second clamping member 66 and that are shaped to fit around a siphon tube. The retention portions 72A and 72B are preferably circular in shape and have a diameter that is proximate to a diameter of a siphon tube to be retained by the siphon tube holder 62. As shown in FIG. 9B, the one or more retention portions 72A and 72B may have differing diameters.

The first clamping member 64 and second clamping member 66 are secured to one another with a hinge pin 74. A spring 76 is preferably located between the first clamping member 64 and the second clamping member 66. The spring 76 is located between the first clamping member 64 and the second clamping member 66 such that the first pad 68 of the first clamping member 64 and the second pad 70 of the second clamping member 66 are biased towards one another.

The advantages of the present invention include, without limitation, that the present invention provides a reservoir of filtered must or fermenting wine, free of skins, seeds, pulp and foam, within the primary fermenter for taking hydrometer readings. The current method for taking hydrometer readings requires the extraction of samples of the fruit juice or fermenting wine from the primary fermenter to a testing container. The present invention provides a reservoir of filtered must or fermenting wine, free of skins, seeds, pulp and foam, for siphoning from the primary fermenter to carboys and holds the siphon hose securely in place within the body of the fermenting wine, below the cap and above the lees. The current method for siphoning from the primary fermenter requires manual control of the position of the siphon hose within the primary fermenter and is subject to plugging by skins, seeds, and pulp. The present invention reduces the process of taking hydrometer readings to a single step, eliminating the extraction of samples for testing. This can reduce the time required to take hydrometer readings from minutes to seconds. The present invention eliminates the need to unplug siphon tubes, thus it significantly reduces the time required for siphoning wine from the primary fermenter to carboys. The present invention securely holds the siphon tube in place to eliminate the need for manual control of the siphon tube within the primary fermenter and frees a hand for another task during siphoning. The present invention eliminates the drips, runs and spills of staining liquids that result from extracting liquids for testing and removing plugged siphon hoses. The present invention provides a quick and easy way to extract clean samples from the primary fermenter. And, by adding significant efficiencies to two important processes performed when fermenting wine, hydrometer measurements and siphoning, the present invention minimizes the overall exposure of the wine to open air and unwanted bacterial contaminants during fermentation.

In a broad embodiment the present invention is an efficient multipurpose device used by winemakers for filtering, siphoning, or as a cap punch.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A hydrometer filter comprising:
    an elongate vessel having a top end and a bottom end that is distal from the top end, the elongate vessel having an inner portion including an open top end and a closed bottom end, the elongate vessel further comprising a plurality of perforations formed therethrough, wherein the perforations are sized to allow fluid to enter the elongate vessel;
    a flange located concentrically around the vessel, the flange located proximate to the top end of the elongate vessel;
    wherein the hydrometer filter is shaped to receive a hydrometer through the open top end of the elongate vessel and to support the hydrometer within a fermentation container for testing of a fluid within the fermentation container.

2. The hydrometer filter of claim 1, further comprising a foot formed on the bottom end of the elongate vessel, wherein the foot has a diameter that is greater than a diameter of the elongate vessel.

3. The hydrometer filter of claim 2, further comprising a vent hole formed through the foot.

4. The hydrometer filter of claim 1, wherein the flange is removably attached around the elongate vessel.

5. The hydrometer filter of claim 1, wherein the flange is integrally formed on the elongate vessel.

6. The hydrometer filter of claim 5, wherein an inner diameter of the vessel tapers in width towards a top end of the vessel.

7. The hydrometer filter of claim 1, the flange further comprising a raised ring formed around the flange.

8. The hydrometer filter of claim 1, further comprising a handle removably attached to the filter.

9. The hydrometer filter of claim 8, wherein the handle is attached to the filter at the flange.

10. The hydrometer filter of claim 8, the flange further comprising one or more apertures formed therethrough, the one or more apertures shaped to receive connectors formed on ends of the handle.

11. The hydrometer filter of claim 1, wherein elongate vessel is cylindrical.

12. The hydrometer filter of claim 1, wherein the perforations have a diameter of approximately ⅛ inches.

13. The hydrometer filter of claim 1, further comprising a siphon tube holder including:
    a first clamping member having a first pad located thereon;
    a second clamping member having a second pad located thereon and one or more retention portions located on an end of the second clamping member; and
    a spring located between the first clamping member and the second clamping member such that the first pad is biased towards the second pad.

14. A hydrometer filter comprising:
    an elongate vessel having a top end and a bottom end that is distal from the top end, the elongate vessel having an inner portion including an open top end and a closed bottom end, the elongate vessel further comprising a plurality of perforations formed therethrough, wherein the perforations are sized to allow fluid to enter the elongate vessel;

a flange located concentrically around the vessel, the flange located proximate to the top end of the elongate vessel;

a foot formed on the bottom end of the elongate vessel, wherein the foot has a diameter that is greater than a diameter of the elongate vessel;

wherein the hydrometer filter is shaped to receive a hydrometer through the open top end of the elongate vessel and to support the hydrometer within a fermentation container for testing of a fluid within the fermentation container.

15. The hydrometer filter of claim 14, further comprising a vent hole formed through the foot.

16. A hydrometer filter comprising:

an elongate vessel having a top end and a bottom end that is distal from the top end, the elongate vessel having an inner portion including an open top end and a closed bottom end, the elongate vessel further comprising a plurality of perforations formed therethrough, wherein the perforations are sized to allow fluid to enter the elongate vessel;

a flange located concentrically around the vessel, the flange located proximate to the top end of the elongate vessel;

a foot formed on the bottom end of the elongate vessel, wherein the foot has a diameter that is greater than a diameter of the elongate vessel; and a handle removably attached to the filter;

wherein the hydrometer filter is shaped to receive a hydrometer through the open top end of the elongate vessel and to support the hydrometer within a fermentation container for testing of a fluid within the fermentation container.

* * * * *